United States Patent [19]

Goh et al.

[11] Patent Number: 4,931,088

[45] Date of Patent: Jun. 5, 1990

[54] NOVEL 2-NITRO-5-(SUBSTITUTED PHENOXY)BENZOHYDROXIMIC ACID DERIVATIVES

[75] Inventors: Atsushi Goh, Ushiku; Keiji Endo; Yuri Yamamoto, both of Ami, all of Japan

[73] Assignee: Mitsubishi Petrochemical Co., Ltd., Tokyo, Japan

[21] Appl. No.: 232,647

[22] Filed: Aug. 16, 1988

[51] Int. Cl.$^5$ .............................................. A01N 33/24
[52] U.S. Cl. ...................................... 71/100; 71/111; 71/114; 558/252; 560/35; 562/440
[58] Field of Search .................... 560/35; 562/440; 71/111, 114, 100; 558/252

[56] References Cited

U.S. PATENT DOCUMENTS

| | | | |
|---|---|---|---|
| 4,484,008 | 11/1984 | Cook, Jr. et al. | 560/35 |
| 4,657,580 | 4/1987 | Krass | 560/35 |
| 4,710,582 | 12/1987 | Phillips | 560/35 |

FOREIGN PATENT DOCUMENTS

| | | | |
|---|---|---|---|
| 63-162666 | 7/1988 | Japan | 560/35 |
| 2049695 | 12/1980 | United Kingdom | 560/35 |

OTHER PUBLICATIONS

Go et al, *Chemical Abstracts*, vol. 108, No. 17778f (1988).

*Primary Examiner*—Bruce D. Gray
*Attorney, Agent, or Firm*—Wenderoth, Lind & Ponack

[57] ABSTRACT

A compound of the formula

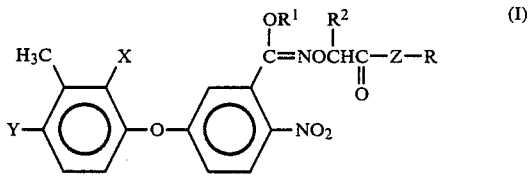

in which each of X and Y represents a halogen atom, R represents a hydrogen atom, a lower alkyl group or an agronomically acceptable soluble salt ion, $R^1$ represents a lower alkyl group, $R^2$ represents a hydrogen atom or a lower alkyl group, and Z represents an oxygen or sulfur atom. This compound is useful as herbicide.

9 Claims, No Drawings

NOVEL 2-NITRO-5-(SUBSTITUTED PHENOXY)BENZOHYDROXIMIC ACID DERIVATIVES

This invention relates to novel 2-nitro-5-(substituted phenoxy)benzohydroximic acid derivatives having herbicidal activity, and more specifically, to compounds of the formula

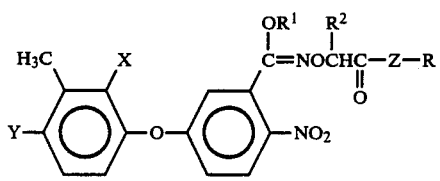

in which each of X and Y represents a halogen atom, R represents a hydrogen atom, a lower alkyl group or an agronomically acceptable soluble salt ion, $R^1$ represents a lower alkyl group, $R^2$ represents a hydrogen atom or a lower alkyl group, and Z represents an oxygen or sulfur atom,
a process for producing these compounds, and herbicides containing them as active ingredients.

The novel benzohydroximic acid derivatives of formula (I) have very superior herbicidal activity against weeds, and exhibit their effects in the preemergence period and in the growth period after emergence, most strongly in the growth period of weeds.

European Patent Application EP-A-155613 discloses diphenyl ether oxime ester derivatives of the following general formula (A) as herbicidally active compounds.

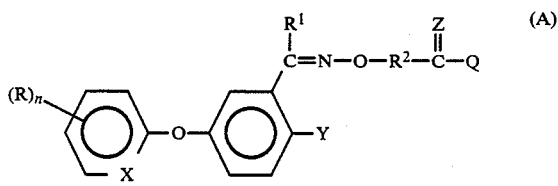

In the general formula (A), X represents CH or N; Y represents a nitro group, a halogen atom, or a cyano group; Z represents an oxygen or sulfur atom; R represents a halogen atom, or a nitro, cyano, alkyl, haloalkyl, alkylthio, haloalkylthio, alkoxy, haloalkoxy, sulfonamide, dialkylsulfonamide, alkylsulfonyl, haloalkylsulfonyl, alkylsulfinyl or haloalkylsulfinyl group; $R^1$ represents a hydrogen or halogen atom, or a cyano, alkyl, haloalkyl, cyanoalkyl, alkoxy, haloalkoxy, cyanoalkoxy, alkylthio, haloalkylthio, cyanoalkylthio, mono- or di-alkylamino, alkylthioalkyl, or mono- or di-alkylaminoalkyl group; $R^2$ represents a $C_1$–$C_6$ alkylene group or an alkenyl group which may be substituted by a haloalkyl, cyanoalkyl or hydroxyl group; n represents 1, 2 or 3; Q represents —$OR^3$ or —$SR^3$; $R^3$ represents an alkoxyalkyl group, a thioalkyl group, a cyanoalkyl group, a cycloalkyl group, a hydroxyalkyl group, a carbalkoxyalkyl group, an alkylthioalkyl group, an aralkyl group, a sulfonamide group, a 4- to 6-membered heterocyclic group containing not more than 3 hetero atoms in the ring, or an alkyl group substituted by a heterocyclic group containing not more than 3 hetero atoms.

In the definition of Q in formula (A). The group $R^3$ in the group —$OR^3$ or —$SR^3$ does not include unsubstituted alkyl groups, nor does it embrace hydrogen and a salt ion. Clearly, therefore, formula (A) does not encompass the compounds of the present invention represented by formula (I).

When in formula (A), CH is selected as X and two halogen atoms and one alkyl group (n=3) are selected as R, the substituted phenoxy moiety of formula (A) could overlap the substituted phenoxy moiety of the compound of formula (I). EP-A-155613, however, totally fails to refer to the selection of such substituents. It only describes compounds having a combination of a halogen atom and a trifluoromethyl group as a preferred group of compounds of formula (A) with regard to the group R. As a specific example of synthesizing these compounds, EP-A-155613 only shows the preparation of a 2-chloro-4-trifluoromethylphenoxy derivative. When an alkoxy group is selected as $R^1$ in formula (A) in EP-A-155613, it can overlap the group —$OR^1$ in the compound of formula (I) provided by this invention. The above EP-A, however, does not at all describe such a selection, and shows only a compound of formula (A) in which $R^1$ is a methyl group in a specific example of synthesis. It only discloses compounds of formula (A) in which $R^1$ is an alkyl or haloalkyl group as a preferred group of compounds of formula (A).

Thus, although EP-A-155613 describes diphenyl ether oxime ester derivatives of formula (A) which can encompass a very large number of compounds, and generally states that they have herbicidal activity, it cannot embrace the compounds of formula (I) in accordance with this invention and gives no disclosure which can suggest the combinations of the groups in the compounds of formula (I). Accordingly, it naturally does not at all suggest the excellent herbicidal activity of the compounds of formula (I).

Use of herbicides is essential to the protection of important crops including corn, soybean, wheat, rice, cotton, beet, rapeseed and sunflower from weeds and to increase the amount of crop harvest. The herbicides are desirably those of the foliage-contacting type which can be applied after emergence according to the type and amount of weeds to be controlled and in reduced dosages in contrast to those of the soil-treating type which are applied before emergence.

The foliage-treating type herbicides are required to have very high selectivity because they also make contact with crops. Thus, very few foliage-treating type herbicides have been developed although many herbicides of the soil-treating type have been synthesized.

Foliage-treating type herbicides now used in soybean farms include, for example, 3-isopropyl-1H-2,1,3-benzothiadiazin (4)-3H-one-2,2-dioxide (bentazone) which is of the diazine type and sodium 5-(2-chloro-4-trifluoromethylphenoxy)-2-nitrobenzoate (acifluorfen sodium) which is of the diphenyl ether type. These herbicides, however, have not proved to be entirely satisfactory in herbicidal activity and herbicidal spectrum, and it has been desired to develop more effective foliage-treating type herbicides.

Examples of foliage-treating type herbicides used in rapeseed farms are 3,6-dichloropicolic acid (clopyralid) of the pyridine type, and 4-chloro-2-oxobenzothiazolin-3-ylacetic acid (benazolin) of the benzothiazoline-type. The herbicidal activities and herbicidal spectra of these compounds are not satisfactory. There is no foliage-treating type diphenyl ether herbicide which has a high level of selectivity for rapeseed and practical utility.

The present inventors made extensive investigations in order to develop diphenyl ether-type herbicides which would overcome the aforesaid technical problems of diphenyl ether-type herbicides of the foliage-treating type, be applicable at reduced rates of application, and have a broad herbicidal spectrum and good selectivity in post-emergence application to useful crops.

These investigations have led to the discovery that novel herbicidally active compounds of formula (I) given above can be synthesized; that these compounds can overcome the technical problems of the prior art and shows a broad range of herbicidal activity and excellent selective herbicidal activity in reduced dosage; and that these herbicidal compounds can exhibit their excellent characteristics in, for example, soil treatment and foliar treatment, particularly the latter.

It is an object of this invention therefore to provide 2-nitro-5-(substituted phenoxy)benzohydroximic acid derivatives of formula (I) given above.

Another object of this invention is to provide processes for producing the compounds of formula (I).

Still another object of this invention is to provide a herbicide comprising a compound of formula (I) as an active ingredient.

The diphenyl ether derivatives of formula (I) provided by this invention are novel compounds not described in the literature. They are characterized in that the hydroximic acid moiety specified in formula (I) which is different from that in the known compounds is attached to the nitro group-containing phenyl ring (to be sometimes referred to as the B ring) of the diphenyl ether derivatives of formula (I) at a position ortho to the nitro group. A further characteristic is that two halogen atoms (X, Y) are bonded to both methyl group of the methyl group-containing phenyl ring (to be sometimes referred to as the A ring) in the diphenyl ether derivative. This structural characteristic is believed to contribute to the excellent herbicidal activity of the diphenyl ether derivatives of formula (I).

The compounds of formula (I) provided by this invention have excellent characteristics that cannot be expected from the prior art. They have selectivity for useful crops including rice, corn, wheat, barley, sorghum, rapeseed, and soybean and a broad herbicidal spectrum and can exhibit their herbicidal activity sufficiently in very low dosage as compared with ordinary herbicides.

The term "lower", used in the present specification and the appended claims to qualify a group or a compound, means that the group or compound so qualified has not more than 6 carbon atoms, preferably not more than 4 carbon atoms.

In the definitions of the substituents in formula (I), the "lower alkyl" may be linear or branched, and includes, for example, methyl, ethyl, n-propyl, iso-propyl, n-butyl, sec-butyl, iso-butyl, n-pentyl, sec-pentyl and n-hexyl.

The "halogen atom" includes fluorine, chlorine, bromine and iodine atoms, and chlorine is preferred.

The "agronomically acceptable soluble salt ion" may be an ion of any of salts of inorganic and organic bases conventional in the field of agricultural chemicals.

In the compounds of formula (I) provided by this invention, X and Y are preferably chlorine, $R^1$ is preferably methyl, and $R^2$ is preferably hydrogen. R is preferably methyl.

Among the compounds given in Table 1 hereinbelow, compounds Nos. 1 and 8 are preferred, and compound No. 1 is especially preferred.

The compounds of formula (I) have one asymmetric carbon atom and may exist in a levorotatory, dextrorotatory or racemic form. The compounds of formula (I) include two stereoisomers (syn-form and anti-form) of formulae (I-a) and (I-b). It should be understood that the formula (I) includes both of these stereoisomers.

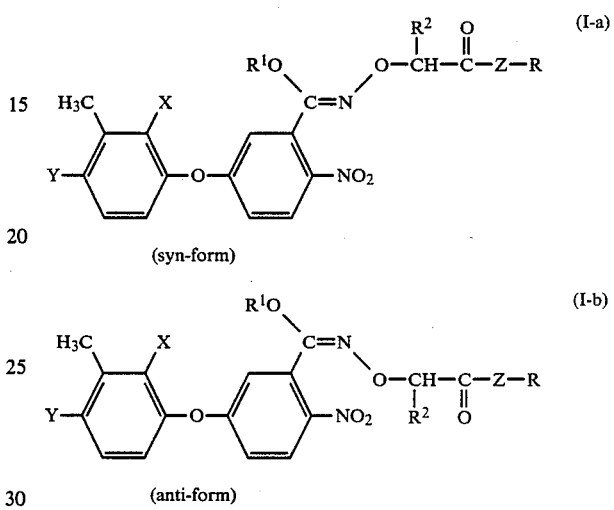

(syn-form)

(anti-form)

Hardly any difference is seen in herbicidal activity between the two stereoisomers, but generally syn-form stereoisomers are believed to be preferred.

The compounds of formula (I) may be produced, for example, by the route shown by the following reaction scheme A.

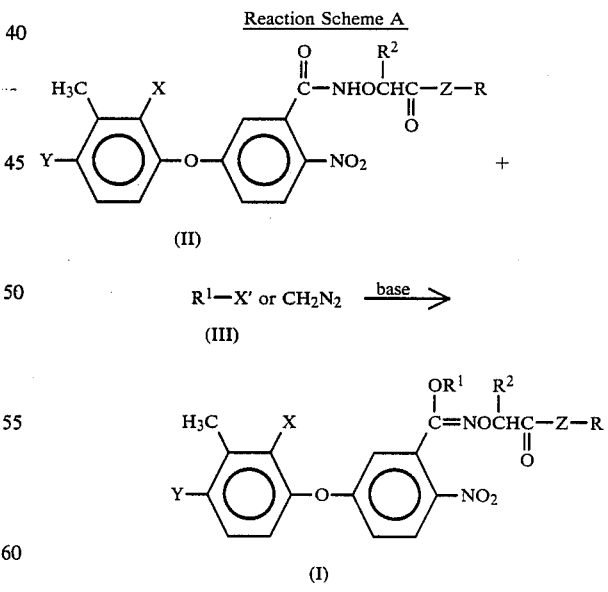

In the formulae, X, Y, Z, R, $R^1$ and $R^2$ are the same as defined above; and X' represents an acid residue such as halogen or the group $-OSO_2R'$ (in which R' represents a substituted or unsubstituted alkyl group, a phenyl group, or an alkoxy group, preferably methyl substituted methyl or methoxy).

According to the above process, the compound of formula (I) in accordance with this invention can be prepared by reacting the compound of formula (II) with the compound of formula (III) in a suitable organic solvent in the presence of a base. This reaction is generally carried out under ice cooling or at a temperature up to the refluxing temperature of the reaction mixture, preferably at room temperature to a temperature of about 80° C. The amount of the compound of formula (III) used relative to the compound of formula (II) is not critical and can be varied widely. Generally, the suitable amount of the compound of formula (III) is 1 to 3 moles, preferably 1 to 2 moles, per mole of the compound of formula (II). Conveniently, the base is used in an amount of usually 1 to 3 equivalents, preferably 1 to 2 equivalents, per mole of the compound of formula (II).

Examples of the solvent used in the above reaction include alcohols such as methanol and ethanol, aromatic hydrocarbons such as benzene and toluene, acetone, acetonitrile, dimethylformamide and dimethyl sulfoxide. Mixtures of these solvents with water may also be used.

Examples of the base used in the above reaction include tertiary amines (e.g., pyridine and triethylamine), sodium hydroxide, potassium hydroxide, sodium carbonate, potassium carbonate, sodium ethylate and sodium hydride.

If diazomethane is used as the compound of formula (II), the use of the base may be omitted.

The reaction may be carried out in a two-layer system. This reaction can be carried out by using a phase-transfer catalyst in an amount of, for example, 1 to 50%, preferably 5 to 30% by weight, based on the compound of formula (II). Examples of the phase transfer catalyst are quaternary ammonium salts such as tetramethyl ammonium bromide, tetrabutyl ammonium bromide and benzyl tributyl ammonium bromide and quaternary phosphonium salts such as tetraphenyl phosphonium bromide.

The compound of formula (II) used as a starting material in the above process can be produced, for example, by the following reaction in which the symbols are as defined above.

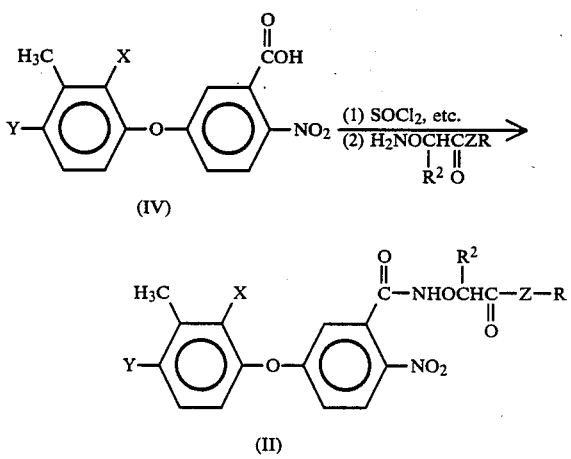

According to this method, 2-nitro-5-(substituted phenoxy)benzoic acid derivative (IV) is converted to an acid chloride with, for example, thionyl chloride, and then reacted with an O-substituted hydroxylamine in the presence of a base in an organic solvent in a customary manner to give the hydroxamic acid derivative (II).

In the reaction, the amount of thionyl chloride used may be varied properly, and is, for example, 1 to 10 equivalents per equivalent of the compound of formula (IV). The reaction temperature can be properly selected, and may be, for example, room temperature to 80° C. In the reaction of the acid chloride with the O-substituted hydroxylamine, the amount of the O-substituted hydroxylamine may be properly varied, and is, for example, 1 to 3 equivalents. The reaction temperature in this reaction may be, for example, under ice cooling to 100° C.

Examples of the organic solvent used include aromatic hydrocarbons such as benzene and toluene; ethers such as tetrahydrofuran and dioxane; acetone; acetonitrile; dimethylformamide; and dimethyl sulfoxide. A mixture of the organic solvent with water may also be used. Examples of the base are pyridine, triethylamine, sodium carbonate, potassium carbonate and sodium hydrogen carbonate.

In the reaction scheme A above, the compound of formula (I) may be isolated and purified by pouring the reaction mixture after the reaction into water and treating it by a conventional method, for example, extraction with an organic solvent, recrystallization, or column chromatography.

The following examples specifically illustrate the compound (I) of the invention and a starting material for it.

EXAMPLE 1

Synthesis of methoxycarbonylmethyl 5-(2,4-dichloro-3-methylphenoxy)-2-nitrobenzohydraxamate (starting material)

34.2 g (0.10 mole) of 5-(2,4-dichloro-3-methylphenoxy)-2-nitrobenzoic acid was dissolved in 50 ml of thionyl chloride, and the solution was heated under reflux for 1.5 hours. The excess of thionyl chloride was evaporated to give an acid chloride.

A solution of the acid chloride in 150 ml of a 1:1 mixture of ether and tetrahydrofuran was added dropwise to a solution of 10.5 g (0.1 mole) of methyl aminooxyacetate and 10.1 g (0.1 mole) of triethylamine in 300 ml of dry ether under ice cooling with stirring over the course of about 20 minutes. Then, the mixture was stirred for 30 minutes under ice cooling and for 1.5 hours at room temperature. The reaction mixture was poured into 300 ml of ice water and extracted with 200 ml of ethyl acetate three times. The extracts were washed with a saturated aqueous solution of sodium chloride and dried over magnesium sulfate. The desiccant was separated by filtration, and the solvent was evaporated. The resulting solid was recrystallized from toluene to give 28.6 g (yield 66.5%) of methoxycarbonylmethyl 5-(2,4-dichloro-3-methylphenoxy)-2-nitrobenzohydroxamate.

EXAMPLE 2

Production of methyl O-methoxycarbonylmethyl-5-(2,4-dichloro-3-methylphenoxy)-2-nitrobenzohydroximate (compound No. 1)

A suspension in 15 ml of dimethylformamide of 2.15 g (5 millimoles) of methoxycarbonylmethyl 5-(2,4-dichloro-3-methylphenoxy)-2-nitrobenzohydroxamate and 1.10 g (8 millimoles) of anhydrous potassium carbonate was heated to 65° to 67° C., and 1.1 g (6 millimoles) of methyl p-toluenesulfonate was added dropwise over about 15 minutes. The mixture was then stirred at the same temperature for 1 hour. The reaction mixture was poured into about 150 ml of ice water, and extracted with 30 ml of ethyl acetate twice. The organic layers were washed with a saturated aqueous solution of sodium chloride and dried over magnesium sulfate. The desiccant was separated by filtration, and the solvent was evaporated. The resulting oily substance was purified by column chromatography (silica gel; n-hexane/ethyl acetate=3/1) to give 630 mg (yield 28.5%) of the desired compound No. 1. It had a melting point of 106.5° to 107.0° C.

Table 1 below shows diphenyl ether derivatives of the invention synthesized by a similar method as in Example 2.

TABLE 1

$$H_3C \underset{Y}{\overset{X}{\bigcirc}}-O-\underset{NO_2}{\bigcirc}-\underset{\underset{O}{\overset{OR^1 \; R^2}{C=NOCHC-Z-R}}}{}$$

| No. | X | Y | $R^1$ | $R^2$ | Z | R | Physical property values |
|---|---|---|---|---|---|---|---|
| 1 | Cl | Cl | Me | H | O | Me | m.p. 106.5–107.0° C. (syn) 90.5–93.0° C. (anti) |
| 2 | Cl | Cl | Me | H | O | Et | |
| 3 | Cl | Cl | Me | H | O | i-Pr | |
| 4 | Cl | Cl | Me | H | O | n-Pr | |
| 5 | Cl | Cl | Me | H | O | n-Bu | |
| 6 | Cl | Cl | Me | H | O | t-Bu | |
| 7 | Cl | Cl | Me | H | O | H | m.p. 158.0–160.0° C. |
| 8 | Cl | Cl | Me | H | S | Me | m.p. 125.5–128.0° C. |
| 9 | Cl | Cl | Me | H | S | Et | |
| 10 | Cl | Cl | Me | H | S | i-Pr | |
| 11 | Cl | Cl | Me | H | S | n-Pr | |
| 12 | Cl | Cl | Me | H | S | n-Bu | |
| 13 | Cl | Cl | Me | H | S | H | |
| 14 | Cl | Cl | Me | H | O | Na | m.p. 164.0–166.0° C. |

Since the compounds of this invention represented by formula (I) have very high herbicidal activity, they show a very high herbicidal efficacy in low dosage. They also have good selectivity for cultivated crops, and are agriculturally useful.

The compounds of this invention can control various weeds occurring in paddies and upland farms in the preemergence period to the growth period after emergence. For example, they can control narrow-leaved and broad-leaved weeds in paddies such as barnyardgrass (*Echinochloa crus-galli*, umbrella plant (*Cyperus difformis*), monochoria (*Monochoria vaginalis*), false pimpernel (*Lindernia pyxidaria*), waterwort (*Elatine triandra*), "kikashigusa" (*Rotala indica*), bulrush (*Scirpus juncoides*), and spikerush (*Eleocharis acicularis*), and narrow-leaved and broad-leaved weeds in upland farms such as crabgrass (*Digitaria sanguinalis*), giant foxtail (*Setaria faberi*), goosegrass (*Eleusine indica*), ricegrass paspalum (*Paspalum orbiculare*), water foxtail (*Alopecurus aequalis*), common chickweed (*Stellaria media*), various species of Polygonum, various species of Amaranthus, velvetleaf (*Abutilon theophrasti*), lambsquarters (*Chenopodium album*), prickly sida (*Sida spinosa*), cocklebur (*Xanthium strumarium*), ragweed (*Ambrosia artemisiifolia*), shepherds-purse (Capsella bursa-pastoris), flexuous bittercress (*Cardamine flexuosa*), common blackjack (*Bidens pilosa*), cleavers (*Galium aparine*) and wild buckwheat (*Polygonum convolvulus*). The compounds of this invention may be used in orchards, mulberry fields and non-agricultural lands.

The compounds of this invention show particularly strong herbicidal activity against broad-leaved weeds growing in upland farms. For example, by foliar treatment in upland farms, they show an excellent herbicidal efficacy against such weeds as green amaranth (*Amaranthus viridis*), common purslane (*Portulaca oleracea*), cocklebur, common blackjack, ragweed, burcucumber (*Sicyos angulatus*), fig-leaved goosefoot (*Chenopodium ficifolium*), lambsquarters, smartweed (*Polygonum lapathifolium*), common chickweed, shepherd's-purse, mouseear chickweed (*Cerastium vulgatum*), jimsonweed (*Datura stramonium*), hemp sesbania (*Sesbania exaltata*), sicklepod (*Cassia tora*), tall morningglory (*Ipomoea purpurea*), black nightshade (*Solanum nigrum*), bullnettle (*Solanum carolinense*), henbit (*Lamium amplexicaule*), plaintain (*Plantago major*), velvetleaf, prickly sida, creeping woodsorrel (*Oxalis corniculata*), cleavers, wild buckwheat, speadwell (*Veronica persica*) and poppy (*Papaver rhoeas*). The compounds of this invention furthermore have selectivity for cultivated plants, and do not substantially cause significant phytotoxicity to gramineous crops such as rice, corn, wheat, barley, sorghum and sugarcane, and broad-leaved crops such as soybean, rapeseed and sunflower.

For use as herbicides, the compounds of this invention may be mixed with agriculturally and horticulturally acceptable carriers or diluents, additives and adjuvants by known techniques and formulated into various forms normally used as agricultural chemicals, for example, a dust, granules, a wettable powder, an emulsifiable concentrate, a soluble powder, a sol, etc. They may be used in admixture or combination with other agricultural chemicals, such as fungicides, insecticides, miticides, other herbicides, plant growth regulating agents, fertilizers, and soil conditioners.

The combined use with another herbicide enables the dosage of the herbicide of this invention to be decreased and permits labor saving. Moreover, the cooperative action of the two chemicals broadens the herbicidal spectrum and the synergistic action of both can be expected to give a higher efficacy.

The carrier or diluent may be any solid or liquid carriers or diluents generally used in the field of agriculture. Solid carries include talc or clays typified by kaolinite, montmorillonite and attapulgite; inorganic materials such as mica, pyrophyllite, pumice, vermicullite, gypsum, calcium carbonate, dolomite, diatomaceous earth, magnesium lime, apatite, zeolite, silicic anhydride and synthetic calcium silicate; organic substances of the plant origin such as soybean meal, tobacco powder, walnut powder, wheat flour, wood powder, starch and crystalline cellulose; natural or synthetic polymeric compounds such as coumarone resins, petroleum resins, alkyd resins, polyvinyl chloride, polyalkylene glycols, ketone resins, ester gum, copal gum and dammar gum; waxes such as carnauba wax and beeswax; and urea. Suitable liquid carriers or diluents include paraffinic or naphthenic hydrocarbons such as kerosene, mineral oils, spindle oil and white oil; aromatic hydrocarbons such as benzene, toluene, xylene, ethylbenzene, cumene and methylnaphthalene; chlorinated hydrocarbons such as carbon tetrachloride, chloroform, trichloroethylene, monochlorobenzene and o-chlorotoluene; ethers such as dioxane and tetrahydrofuran; ketones such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, n-hexanol, ethylene glycol, diethylene glycol, cyclohexanol and benzyl alcohol; ether alcohols such as ethylene glycol ethyl ether, ethylene glycol phenyl ether, diethylene glycol ethyl ether and diethylene glycol butyl ether; polar solvents such as dimethyl formamide and dimethyl sulfoxide; and water.

Surface-active agents and other adjuvants may be used to emulsify, disperse, wet, spread or bind the compound of this invention, adjust its disintegrability, stabilize the active ingredients of the herbicide, improve the flowability of the herbicide, prevent corrosion, or otherwise. The surface-active agents may be nonionic, anionic, cationic and amphoteric. Usually, nonionic and anionic surface-active agents are suitable. Suitable nonionioc surface-active agents include, for example, polyaddition products of ethylene oxide with higher alcohols such as lauryl alcohol, stearyl alcohol and oleyl alcohol; polyaddition products of ethylene oxide with alkylphenols such as iso-octylphenol and nonylphenol; polyaddition products of ethylene oxides with alkylnaphthols such as butylnaphthol and octylnaphthol; polyaddition products of ethylene oxide with higher fatty acids such as palmitic acid, stearic acid and oleic acid; polyaddition products of ethylene oxide with mono- or di-alkylphosphoric acids such as stearylphosphoric acid and dilaurylphosphoric acid; polyaddition products of ethylene oxide with amine compounds such as dodecylamine and stearamide; higher fatty acid esters of polyhydric alcohols such as sorbitan, and polyaddition products of ethylene oxide with these esters; and a polyaddition product of ethylene oxide with propylene oxide. Suitable anionic surface-active agents include, for example, alkylsulfuric ester salts such as sodium laurylsulfate and oleyl sulfate amine salt; alkylsulfonic acid salts such as sodium 2-ethylhexenesulfonate; and arylsulfonic acid salts such as sodium isopropylnaphthalenesulfonate, sodium methylenebisnaphthalenesulfonate, sodium ligninesulfonate and sodium dodecylbenzenesulfonate.

To improve the properties of the formulated herbicide and increase its herbicidal efficacy, the compound of the invention may also be used in combination with other adjuvants including such polymeric compounds as casein, gelatin, albumin, glue, sodium alginate, carboxymethyl cellulose, methyl cellulose, hydroxyethyl cellulose and polyvinyl alcohol.

The above carriers or diluents and various adjuvants may be used singly or in suitable combinations depending upon the form of the formulated herbicide, the place and time of application, etc.

The proportion of the compound of the invention as an active ingredient in the formulated herbicide may be varied with the form of the herbicide. For example, it is usually from 0.1 to 99% by weight, preferably from 1 to 80% by weight.

The dust usually contains 1 to 25% by weight of the active ingredient and the remainder being a solid carrier.

The wettable powder usually contains 25 to 90% by weight of the active ingredient and the remainder being a solid carrier and a dispersing and wetting agent and optionally a protective colloid, a thixotropic agent, a defoamer, etc.

The granules usually contain 1 to 35% by weight of the active ingredient and the remainder being mostly a solid carrier. The active ingredient is uniformly mixed with the solid carrier, or uniformly fixed to, or adsorbed on, the surface of the solid carrier. The granules have a particle diameter of about 0.2 to 1.5 mm.

The emulsifiable concentrate usually contains 1 to 30% by weight of the active ingredient, about 5 to 20% by weight of an emulsifier and the remainder being a liquid carrier and optionally a corrosion inhibitor.

The compound of formula (I) provided by this invention may be applied directly as a herbicide or in any desired form such as the formulations described above.

The herbicide of this invention can be applied to various weeds occurring in paddies and upland farms in a preemergence period or in a growth period after emergence, preferably to weeds in a growth period. Application to upland farms is especially suitable.

In controlling weeds by using the compounds of this invention, a herbicidally effective amount of the compound of this invention may be applied to the soil in the locus where weeds before emergence are desired to be controlled, or directly to weeds after emergence.

The rate of application can be low because the compounds of this invention have very high herbicidal activity. It may be properly varied with the type of weeds to be controlled, the stage of growth, the place of application, the time of application, weather, etc. Generally, the rate of application is about 0.01 to 10,000 g, preferably about 0.1 to 5,000 g, per hectare as the amount of the compound of general formula (I) (the amount of the active ingredient). More preferably, it is about 50 to 2,000 g/ha before emergence (soil treatment), and about 1 to 100 g/ha after emergence (foliar treatment).

The following Formulation Examples show some examples of formulating the compound of this invention. All parts herein are by weight.

FORMULATION EXAMPLE 1

| Granules:- | |
|---|---|
| Ingredient | Parts |
| Compound of formula (I) (e.g., compound No. 1) | 5 |
| Bentonite | 50 |
| Talc | 40 |
| Sodium dodecylbenzenesulfonate | 2 |
| Sodium ligninsulfonate | 2 |
| Polyoxyethylene alkyl aryl ether | 1 |

The above ingredients were thoroughly mixed, and a suitable amount of water was then added. The mixture was kneaded and granulated by a granulator to give 100 parts of granules.

FORMULATION EXAMPLE 2

| Wettable powder:- | |
|---|---|
| Ingredient | Parts |
| Compound of formula (I) (e.g., compound No. 1) | 20 |
| Clay | 70 |
| White carbon | 5 |
| Sodium ligninsulfonate | 3 |
| Sodium dodecylbenzenesulfonate | 2 |

The above ingredients were mixed and kneaded and pulverized uniformly by a kneader to give 100 parts of a wettable powder.

FORMULATION EXAMPLE 3

| Emulsifiable concentrate:- | |
|---|---|
| Ingredient | Parts |
| Compound of formula (I) (e.g., compound No. 1) | 20 |
| Cyclohexanone | 70 |
| Calcium dodecylbenzenesulfonate | 5 |
| Polyoxyethylene alkyl aryl ether | 5 |

The above ingredients were uniformly mixed and dissolved to form 100 parts of an emulsifiable concentrate.

FORMULATION EXAMPLE 4

| Flowable composition:- | |
|---|---|
| Ingredient | Parts |
| Compound No. 1 | 20 |
| Polyoxyethylene alkylaryl ether | 2 |
| Calcium dodecylbenzenesulfonate | 3 |
| Silicone-type defoamer | 0.2 |
| Propylene glycol | 8 |
| 2% Aqueous solution of guar gum | 12 |
| Water (remainder) | 54.8 |

The above ingredients were mixed and pulverized uniformly for several hours by a wet-type pulverizer to give 100 parts of a flowable composition.

Other forms of the formulation of the compound of this invention could be prepared substantially in accordance with the above Formulation Examples.

The following Test Examples demonstrate the excellent herbicidal activity of the compounds of formula (I) provided by this invention.

TEST EXAMPLE 1

Foliar treatment

Upland farm soil was filled in square pots (30×30×8 cm). Seeds of various crops and weeds indicated in Table 2 were sown each in fixed amounts, and grown in a greenhouse until the plants grew to the 1.5- to 3-leaf stage (18th day after sowing).

Each of the test compounds was dissolved in a mixture of acetone and water (1:1) containing 0.2% of Tween 20 and applied uniformly to the foliage of the plants at each of the rates of application shown in Table 2.

Twenty-one days after the application, the herbicidal efficacy on the weeds and the degree of phytotoxicity to the crops were evaluated on the following standards, and the results are shown in Table 2.

| | Rating Standards (11 rates) | |
|---|---|---|
| Rating | Herbicidal efficacy (herbicidal rate, %, based on a non-treated area) | Phytotoxicity to crops (phytotoxicity rate, %, based on a non-treated area) |
| 0 | 0 | Same as left |
| 1 | over 0 to 10 | |
| 2 | over 10 to 20 | |
| 3 | over 20 to 30 | |
| 4 | over 30 to 40 | |
| 5 | over 40 to 50 | |
| 6 | over 50 to 60 | |
| 7 | over 60 to 70 | |
| 8 | over 70 to 80 | |
| 9 | over 80 to 90 | |
| 10 | over 90 to 100 (withered) | |

The alphabets in the columns of "Herbicidal efficacy" and "Phytotoxicity to crops" represent the following weeds and crops.

A: crabgrass
B: green amaranth
C: velvetleaf
D: jimsonweed
E: tall morningglory
F: cocklebur
G: corn
H: wheat
I: rice
J: soybean
K: rapeseed.

TABLE 2

| Compound No. | Amount of the active ingredient (g/ha) | Herbicidal efficacy | | | | | | Phytotoxicity to crop | | | | |
|---|---|---|---|---|---|---|---|---|---|---|---|---|
| | | A | B | C | D | E | F | G | H | I | J | K |
| 1 | 90 | 6 | 10 | 10 | 10 | 10 | 10 | 0 | 0 | 1 | 0 | 0 |
| | 30 | 4 | 10 | 10 | 10 | 10 | 4 | 0 | 0 | 0 | 0 | 0 |
| 7 | 90 | 6 | 10 | 10 | 10 | 10 | 10 | 0 | 0 | 1 | 0 | 0 |
| | 30 | 5 | 10 | 9 | 10 | 10 | 8 | 0 | 0 | 0 | 0 | 0 |
| 14 | 90 | 8 | 10 | 10 | 10 | 10 | 10 | 0 | 0 | 1 | 0 | 0 |
| | 30 | 5 | 10 | 10 | 10 | 10 | 10 | 0 | 0 | 0 | 0 | 0 |
| 9 | 90 | 8 | 10 | 10 | 10 | 10 | 10 | 1 | 1 | 1 | 0 | 0 |
| | 30 | 8 | 10 | 10 | 10 | 10 | 7 | 0 | 0 | 0 | 0 | 0 |
| Comparison a | 300 | 8 | 10 | 10 | 10 | 10 | 10 | 5 | 3 | 2 | 2 | 10 |
| | 90 | 6 | 10 | 10 | 10 | 9 | 7 | 1 | 2 | 1 | 0 | 10 |
| Comparison b | 90 | 8 | 10 | 10 | 10 | 10 | 10 | 3 | 6 | 6 | 8 | 10 |
| | 30 | 5 | 10 | 10 | 10 | 10 | 7 | 0 | 3 | 3 | 2 | 10 |
| Non-treated | | 0 | 0 | 0 | 0 | 0 | 0 | | | | | |

Note to Table 2
a in the column of "Compound No." represents sodium 5-(2'-chloro-4'trifluoromethylphenoxy)-2-nitrobenzoate.
b in the column of "Compound No." represents methyl 5-(2'-chloro-4'-trifluoromethylphenoxy)-2-nitroacetophenoneoxime-O-acetate.

We claim:

1. A compound of the formula

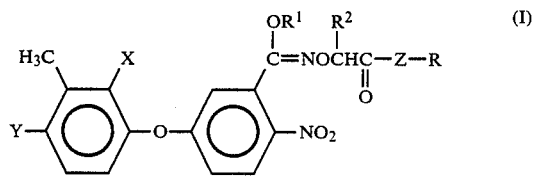

in which each of X and Y represents a halogen atom, R represents a hydrogen atom, a lower alkyl group or an agronomically acceptable soluble salt ion, $R^1$ represents a lower alkyl group, $R^2$ represents a hydrogen atom, and Z represents an oxygen or sulfur atom.

2. The compound of claim 1 in which both X and Y are chlorine atoms.

3. The compound of claim 1 in which $R^1$ is a methyl group.

4. The compound of claim 1 in which R is a methyl group.

5. The compound of claim 1 which is in a syn form.

6. The compound of claim 1 which is methyl O-methoxycarbonylmethyl-5-(2,4-dichloro-3-methylphenoxy)-2-nitrobenzohydroximate.

7. The compound of claim 2 wherein R is a lower alkyl group, $R^1$ represents methyl and Z represents an oxygen atom.

8. A herbicidal composition comprising an effective amount of the compound of formula (I) set forth in claim 1 and an agriculturally and horticulturally acceptable carrier or diluent.

9. A method of controlling weeds which comprises applying an effective amount of the compound of formula (I) set forth in claim 1 to the locus where the weeds are to be controlled, or to the weeds to be controlled.